(12) United States Patent
Sun

(10) Patent No.: US 9,709,624 B2
(45) Date of Patent: Jul. 18, 2017

(54) AUTOMATIC TEST SYSTEM AND METHOD

(71) Applicants: INVENTEC (PUDONG) TECHNOLOGY CORPORATION, Shanghai (CN); INVENTEC CORPORATION, Taipei (TW)

(72) Inventor: Meng Sun, Shanghai (CN)

(73) Assignees: INVENTEC (PUDONG) TECHNOLOGY CORPORATION, Shanghai (CN); INVENTEC CORPORATION, Taipei (TW)

( * ) Notice: Subject to any disclaimer, the term of this patent is extended or adjusted under 35 U.S.C. 154(b) by 728 days.

(21) Appl. No.: 14/246,938

(22) Filed: Apr. 7, 2014

(65) Prior Publication Data

US 2015/0142365 A1  May 21, 2015

(30) Foreign Application Priority Data

Nov. 21, 2013  (CN) .......................... 2013 1 0594144

(51) Int. Cl.
*G01D 3/00*     (2006.01)
*G01R 31/28*    (2006.01)
*G06F 11/30*    (2006.01)
*G01N 35/00*    (2006.01)
*H04R 29/00*    (2006.01)

(52) U.S. Cl.
CPC .... *G01R 31/2834* (2013.01); *G01N 2035/009* (2013.01); *G01N 2035/0091* (2013.01); *G01N 2035/00752* (2013.01); *H04R 29/00* (2013.01)

(58) Field of Classification Search
CPC .................................................. G01R 31/2834
See application file for complete search history.

(56) References Cited

U.S. PATENT DOCUMENTS 8,719,419 B2 *   5/2014  Usmani .............. G06F 11/3688
                                                     709/225
2006/0229018 A1 * 10/2006 Mlinarsky .......... H04B 17/0087
                                                     455/67.11

* cited by examiner

*Primary Examiner* — Phuong Huynh
(74) *Attorney, Agent, or Firm* — Bacon & Thomas, PLLC

(57) ABSTRACT

System and method of dividing a window according to trail are provided. The system and the method record the moving trail of an indicating signal and then divide the window according to the moving trail into two independent blocks to display the file separately. By completing the procedures, the system and the method enable a user to divide a window according to a user-defined direction, and therefore further enhance the contrast effect between different parts of a file.

16 Claims, 6 Drawing Sheets

AUTOMATIC TEST SYSTEM AND METHOD

BACKGROUND OF THE RELATED ART

Technical Field

The present invention relates to a test system and method and particularly to an automatic test system and method by using a smart interaction device capable of providing a barcode, picture and sound for verification.

Related Art

Recently, with prevalence and vigorous development of semiconductor technology, the electronic products have increasingly higher productivity efficiency. How to simultaneously promote a test efficiency of the electronic products has become an issue every producer is eager to overcome.

Generally, in testing an electronic product, the to-be-tested electronic product (unit under test, UUT) is arranged to connect with a test terminal, and the test terminal performs a series of operations and tests on the test case according to various process flows. However, in some cases, such as testing a microphone to see if it may receive sounds, testing a loudspeaker to see if it may broadcast sounds, and testing a display to see if its outputted color is correct. Since this method may not determine directly if the test case is normal, the test requires to be performed in a manual or additional manner, resulting in a poor test efficiency.

In view of this, there has been a way proposed by increasing sensors to detect some test items which can not be directly determined by an electric signal. However, these sensors may not move as the electronic product varies, it requires to throw out a large of time on re-arranging the positions of the sensors for adaptation of use of the unit under test product before the test. Therefore, this manner still has the issue of poor test efficiency.

In view of the above, it may be known that there has been long the issue of poor test efficiency, and it is quite a need to set forth a technical means to improve this issue.

SUMMARY

The present invention discloses an automatic test system and method.

According to a first embodiment of the present invention, the automatic test system comprises a smart interaction device, receiving a first control signal and scanning a barcode of a unit under test, taking a picture of the unit under test, recording a sound generated by the unit under test and playing a sound preset in the smart interaction device according to the first control signal; a fixture device, receiving a second control signal and moving the smart interaction device installed therein according to the second control signal; a test terminal, receiving and executing a test script to automatically test the unit under test, and verifying the barcode, picture and sound of the unit under test received from the smart interaction device to generate a test result; and a server, transmitting the test script pre-stored in the test script to the test terminal, generating the first and second control signals, and transmitting the first and second control signals to the smart interaction device and the fixture device, respectively.

According to a second embodiment of the present invention, the automatic test system comprises a smart interaction device, receiving a first control signal and a second control signal, and scanning a barcode of a unit under test according to the first control signal, and taking a picture of the unit under test, recording a sound generated by the unit under test and playing a sound preset in the smart interaction device according to the second control signal; a fixture device, receiving a third control signal and moving the smart interaction device installed therein according to the third control signal; a test terminal, receiving and executing a test script to automatically test the unit under test, and generating a second test signal to receive the picture and sound of the unit under test received from the smart interaction device to generate a test result; and a server, generating the first control signal and transmitting the first control signal to the smart interaction device, receiving the barcode of the unit under test from the smart interaction device to screen out a test script to be transmitted to the test terminal, and generating the third control signal to transmit to the fixture device.

According to a first embodiment of the present invention, the automatic test method applied onto an environment having a smart interaction device, a fixture device, a test terminal and a server, comprises steps of generating a first control signal and transmitting the first control signal to the smart interaction device, and generating a third control signal and transmitting the third control signal to the fixture device; moving the smart interaction device installed in the fixture device according to the third control signal by the fixture device; scanning a barcode of a unit under test by the smart interaction device according to the first control signal; receiving the barcode of the unit under test from the smart interaction device by the server to screen out a test script to be transmitted to the test terminal; receiving and executing the test script by the test terminal to automatically test the unit under test, and generating a second control signal to the smart interaction device; taking a picture of the unit under test, recording a sound generated by the unit under test and playing a sound preset in the smart interaction device by the smart interaction device according to the second control signal; and receiving and verifying the picture and sound from the smart interaction device by the test terminal to generate a test result.

According to a second embodiment of the present invention, the automatic test method applied onto an environment having a smart interaction device, a fixture device, a test terminal and a server comprises steps of generating a first control signal and transmitting the first control signal to the smart interaction device, and generating a third control signal and transmitting the third control signal to the fixture device; moving the smart interaction device installed in the fixture device according to the third control signal by the fixture device; scanning a barcode of a unit under test by the smart interaction device according to the first control signal; receiving the barcode of the unit under test from the smart interaction device by the server to screen out a test script to be transmitted to the test terminal; receiving and executing the test script by the test terminal to automatically test the unit under test, and generating a second control signal to the smart interaction device; taking a picture of the unit under test, recording a sound generated by the unit under test and playing a sound preset in the smart interaction device by the smart interaction device according to the second control signal; and receiving and verifying the picture and sound from the smart interaction device by the test terminal to generate a test result.

The system and method of the present invention has the difference as compared to the prior art that the present invention drives the fixture device, smart interaction device and test terminal through a control signal, so that the smart interaction device installed in the fixture device scans the barcode and picture of the unit under test and records the sound and plays the sound preset in the smart interaction device, so as to provide the test terminal to verify when executing an automatic test process to generate a test result.

By means of the above technical means, the present invention may achieve in a result of promotion of a test efficiency.

BRIEF DESCRIPTION OF THE DRAWINGS

The invention will become more fully understood from the detailed description given herein below illustration only, and thus is not limitative of the present invention, and wherein.

DETAILED DESCRIPTION

The present invention will be apparent from the following detailed description, which proceeds with reference to the accompanying drawings, wherein the same references relate to the same elements.

Prior to the description of the automatic test system and method of the present invention, nouns defined privately in the present invention are explained. In the present invention, the unit under test is a to-be-tested electronic device, such as a motherboard, and a display component. In addition, the smart interaction device mentioned in the present innovation comprises a smart cell phone, a digital personal assistant and a tablet computer comprises a photographing element, a sound receiving element, a loudspeaker, and a wireless transmitter device.

Figure 1:
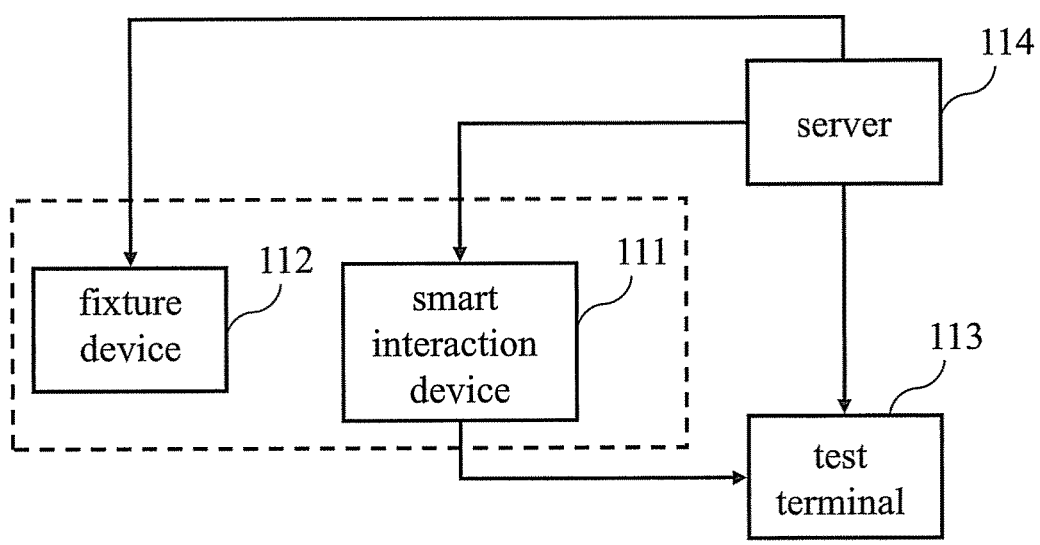
FIG. 1 is a systematic block diagram of an automatic test system according to the present invention.

In the following, the automatic test system and method according to the present invention is further described with reference to the figures. Referring to FIG. 1, in which the systematic block diagram of the automatic test system is illustrated. The system comprises a smart interaction device 111, a fixture device 112, a test terminal 113 and a server 114. The smart interaction device 111 is used to receive a first control signal, and scan a barcode of a unit under test, take a picture of the unit under test, record a sound generated by the unit under test and play a sound of the smart interaction device. In real implementation, assume the first control signal is a binary signal "00", and which may trigger a photographing element to scan the barcode of the unit under test, such as a quick response code (QR code). Assume the first control signal is a binary signal "01", and which may trigger the photographing element to take the picture of the unit under test.

Assume the first control signal is a binary signal "10", and which may trigger the sound receiving element to record the sound generated by unit under test. Assume the first control signal is a binary signal "11", and which may trigger the loudspeaker to play the sound preset in the smart interaction device 111. In addition, these barcode taken and sounds recorded and played may be processed through a processor, and may be transmitted wirelessly.

The fixture device 112 is used to receive a second control signal, and move the smart interaction device 111 installed in the fixture device 112 according to the second control signal. In real implementation, the fixture device 112 comprises a fixation element, a linear sliding rail, a controller and a stepping motor, enabling the smart interaction device 111 to move in a two dimensional space or a three dimensional space. Afterwards, figures are illustrated to make a detailed description of the fixture device 112.

The test terminal 113 is used to receive a test script, and then execute the test script to automatically test the test unit, and verify the barcode, picture and sound of the unit under test received from the smart interaction device to generate a test result. In real implementation, reception of the test script may be implemented wirelessly. As to the automatic test based on the test script, it belongs to the prior art, and thus omitted herein for clarity.

The server 114 is used to transmit the test script prestored to the test terminal 113, and generate a first control signal and a second control signal, in which the first control signal is transmitted to the smart interaction device 111 and the second control signal is transmitted to the fixture device 112. By means of the first and second control signals, the smart interaction device 111 and the fixture device 112 may be controlled, so that the smart interaction device 111 may be moved to the test unit to scan the barcode, take the picture, record the sound and play the sound preset in the smart interaction device 111.

Figure 2:
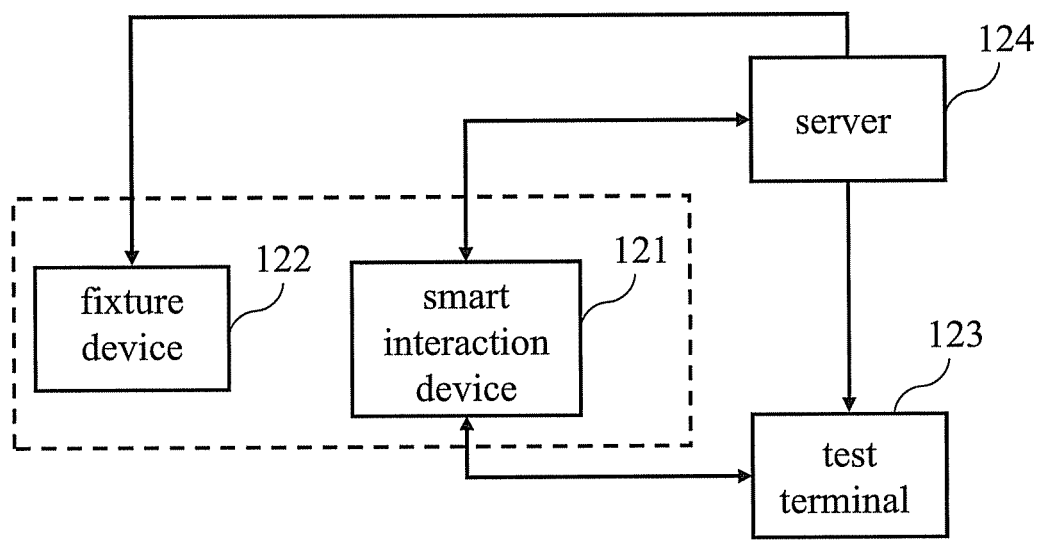
FIG. 2 is a systematic block diagram of the other automatic test system according to the present invention.

Thereafter, Referring to FIG. 2, in which a systematic block diagram of the other automatic test system according to the present invention is shown. The system comprises a smart interaction device 121, a fixture device 122, a test terminal 123, and a server 124. The smart interaction device 121 is used to receive a first control signal and a second control signal. The first control signal is used as a basis for scanning a barcode of the unit under test, and the second control signal for taking the picture, recording the sound generated by the unit under test and the sound preset in the smart interaction device 121. The smart interaction device 121 and the smart interaction device 111 shown in FIG. 1 have the difference that the smart interaction device 121 may transmit the barcode scanned from the unit under test to the server 124, and receive a second control signal from the test terminal 123 to trigger to take the picture of the unit under test, record the sound generated by the unit under test and play the sound preset in the smart interaction device 121.

The fixture device 122 is used to receive a third control signal, and move the smart interaction device 121 installed in the fixture device 122 according to the third control signal. The fixture device 122 is similar to the fixture device 113 shown in FIG. 1, and thus omitted herein for clarity.

The test terminal 123 is used to receive a test script, and execute the test script to automatically test the unit under test. Thereafter, a second test signal is used to verify the picture and sound of the unit under test received from the smart interaction device 121 to generate a test result. The test terminal 123 has the difference as compared to the test terminal 112 schematically shown in FIG. 1 that the test terminal 123 may generate a second test signal, and transmit the second test signal to the smart interaction device 121, so that the smart interaction device 121 may take a picture of the unit under test and record the sound generated by the unit under test.

The server 124 is used to generate a first control signal to transmit the first control signal to the smart interaction device 121, receive the barcode of the unit under test from the smart interaction device 121 to screen out a script to be transmitted to the test terminal 123, and generate the third control signal to transmit to the fixture device 122. The server 124 and the server 114 schematically shown in FIG. 1 have the difference that the server 124 only finishes the barcode scanning by controlling the smart interaction device 121 at a prior stage of the test, and it is the test terminal 123 used to contour the smart interaction device 121 in the succeeding test. In real implementation, multiple different test scripts of the units under test may be restored in the server 124, and screen out the corresponding test script according to the barcode of the unit under test.

Figure 3:
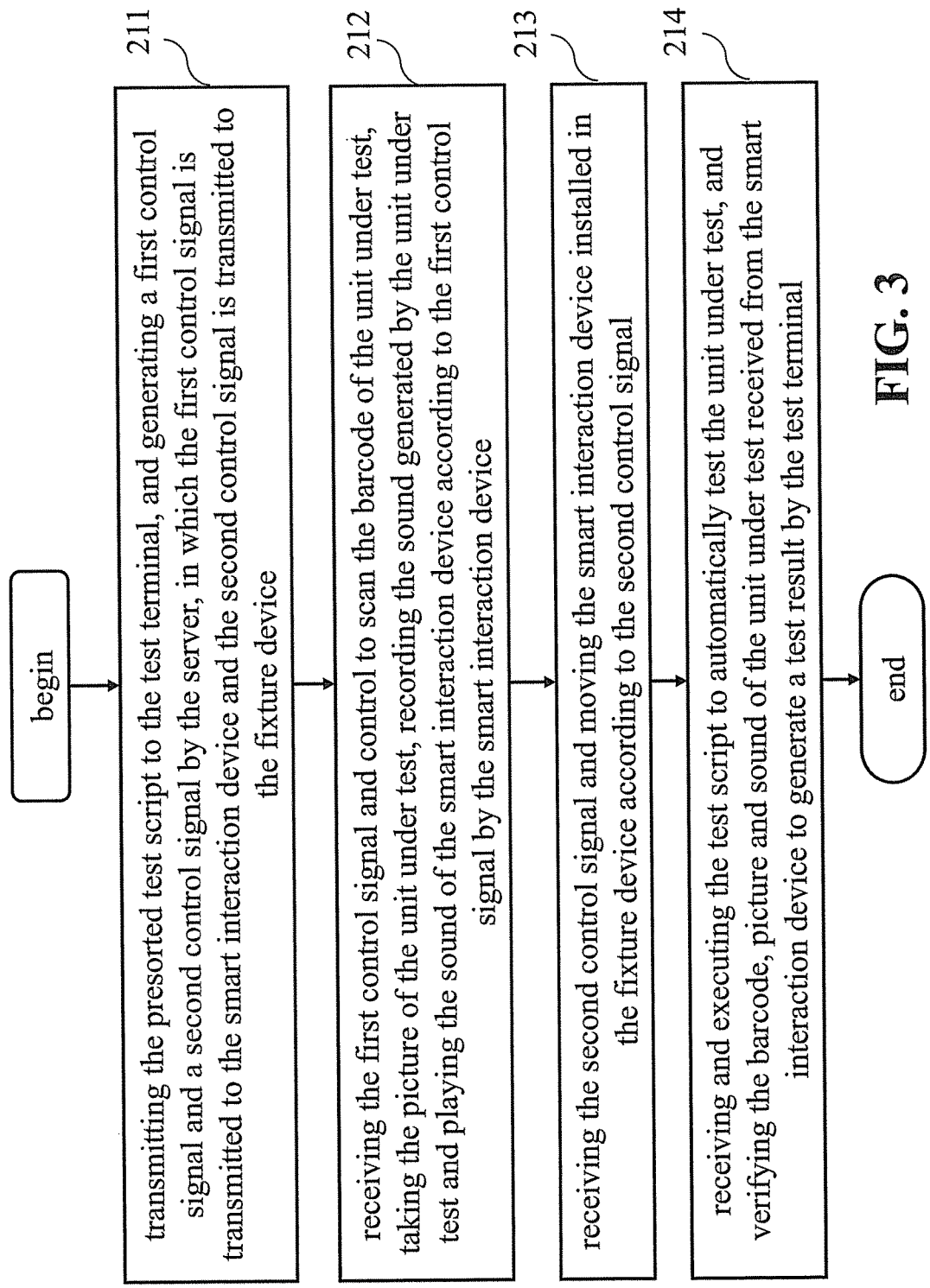
FIG. 3 is a flowchart of an automatic test method according to the present invention.

Thereafter, referring to FIG. 3, in which a flowchart of an automatic test method according to the present invention is shown. The method comprises the following steps. The server 114 transmits the presorted test script to the test terminal 113, and generates a first control signal and a second control signal, in which the first control signal is transmitted to the smart interaction device 111 and the second control signal is transmitted to the fixture device 112 (Step 211). The smart interaction device 111 receives the first control signal and control to scan the barcode of the unit under test, take the picture of the unit under test, record the sound generated by the unit under test and play the sound of the smart interaction device 111 according to the first control signal (Step 212).

The fixture device 112 receives the second control signal and move the smart interaction device 111 installed in the fixture device 112 according to the second control signal (Step 213). The test terminal 113 receives and executes the test script to automatically test the unit under test, and verifies the barcode, picture and sound of the unit under test received from the smart interaction device 111 to generate a test result (Step 214).

By means of the above steps, the control signal may be used to drive the fixture device, smart interaction device and test terminal, so that the smart interaction device 111 installed in the fixture device 112 may scan the barcode and picture of the test unit, record the sound, and play the sound preset in the smart interaction device 111, so as to provide the test terminal 113 to verify in the execution of the automatic test process and generate a test result.

The fixture device 122 is used to receive a third control signal, and move the smart interaction device 121 installed in the fixture device 122 according to the third control signal. The fixture device 122 is similar to the fixture device 113 shown in FIG. 1, and thus omitted herein for clarity.

The test terminal 123 is used to receive a test script, and execute the test script to automatically test the unit under test. Thereafter, a second test signal is used to verify the picture and sound of the unit under test received from the smart interaction device 121 to generate a test result. The test terminal 123 has the difference as compared to the test terminal 112 schematically shown in FIG. 1 that the test terminal 123 may generate a second test signal, and transmit the second test signal to the smart interaction device 121, so that the smart interaction device 121 may take a picture of the unit under test and record the sound generated by the unit under test.

The server 124 is used to generate a first control signal to transmit the first control signal to the smart interaction device 121, receive the barcode of the unit under test from the smart interaction device 121 to screen out a script to be transmitted to the test terminal 123, and generate the third control signal to transmit to the fixture device 122. The server 124 and the server 114 schematically shown in FIG. 1 have the difference that the server 124 only finishes the barcode scanning by controlling the smart interaction device 121 at a prior stage of the test, and it is the test terminal 123 used to control the smart interaction device 121 in the succeeding test. In real implementation, multiple different test scripts of the units under test may be restored in the server 124, and screen out the corresponding test script according to the barcode of the unit under test.

Figure 4:
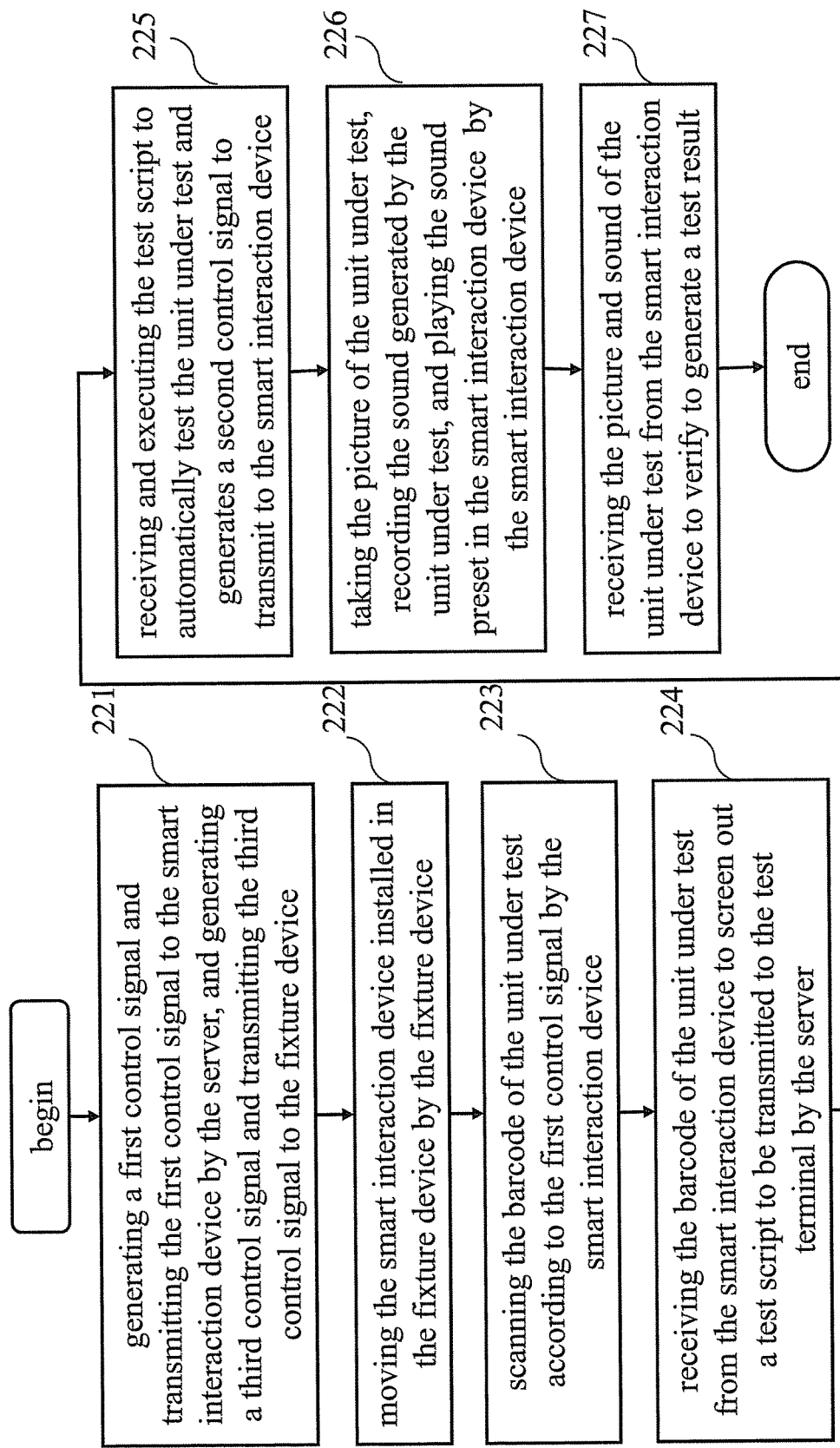
FIG. 4 is a flowchart of the other automatic test method according to the present invention.

As shown in FIG. 4, in which a flowchart of the other automatic test method according to the present invention is shown. The method is applied onto an environment having a smart interaction device 121, a fixture device 122, a test terminal 123, and a server 124. The method comprises the following steps. The server 124 generates a first control signal and transmits the first control signal to the smart interaction device 121, and generates a third control signal and transmits the third control signal to the fixture device 122 (Step 221). The fixture device 122 moves the smart interaction device 121 installed in the fixture device 122 (Step 222). The smart interaction device 121 scans the barcode of the unit under test according to the first control signal (Step 223). The server 124 receives the barcode of the unit under test from the smart interaction device 121 to screen out a test script to be transmitted to the test terminal 123 (Step 224).

The test terminal 123 receives and executes the test script to automatically test the unit under test and generates a second control signal to transmit to the smart interaction device 121 (Step 225). The smart interaction device 121 takes the picture of the unit under test, records the sound generated by the unit under test, and plays the sound preset in the smart interaction device 121 (Step 226). The test terminal 123 receives the picture and sound of the unit under test from the smart interaction device 121 to verify to generate a test result (Step 227).

By means of the above steps, the fixture device 122, the smart interaction device 121 and the test terminal 123 may be similarly driven by control signals, so that the smart interaction device 121 installed in the fixture device 122 scans the barcode and picture of the unit under test, and records the sound and play the sound preset in the smart interaction device 121, so as to provide the test terminal 123 to verify in the execution of the automatic test process and generate a test result.

Figure 5:
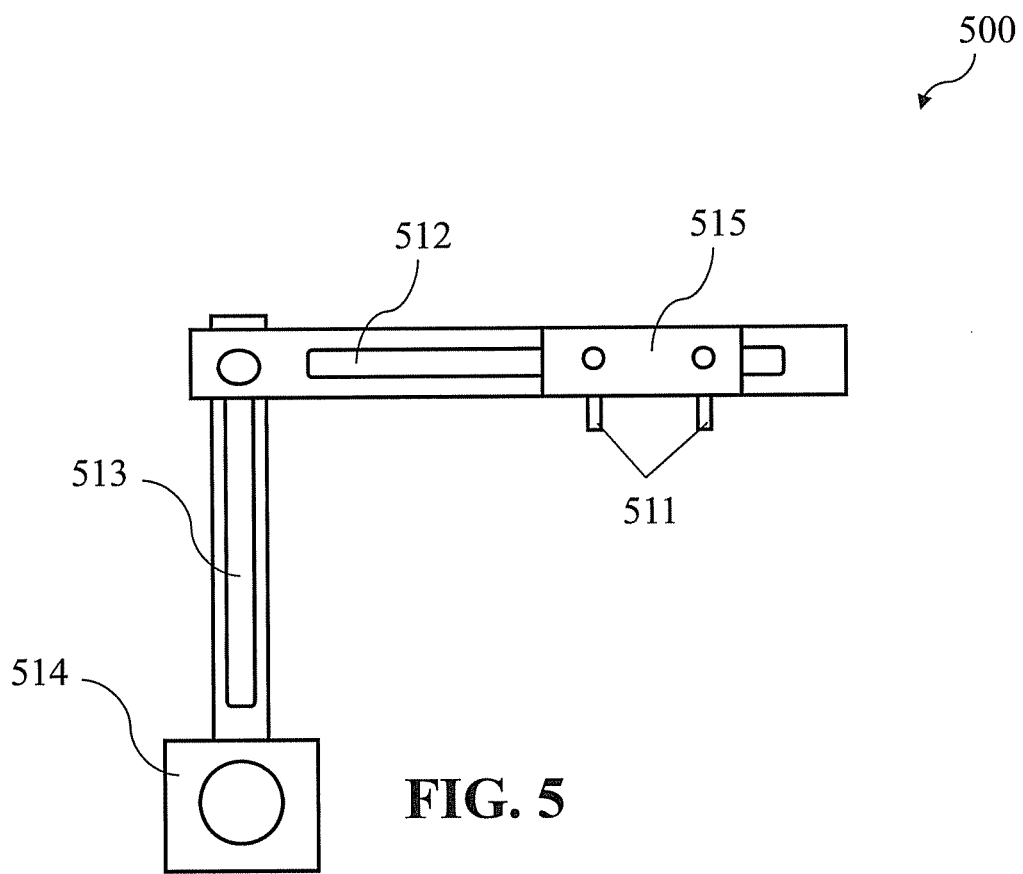
FIG. 5 is a schematic diagram of a fixture device according to the present invention.
Figure 6:
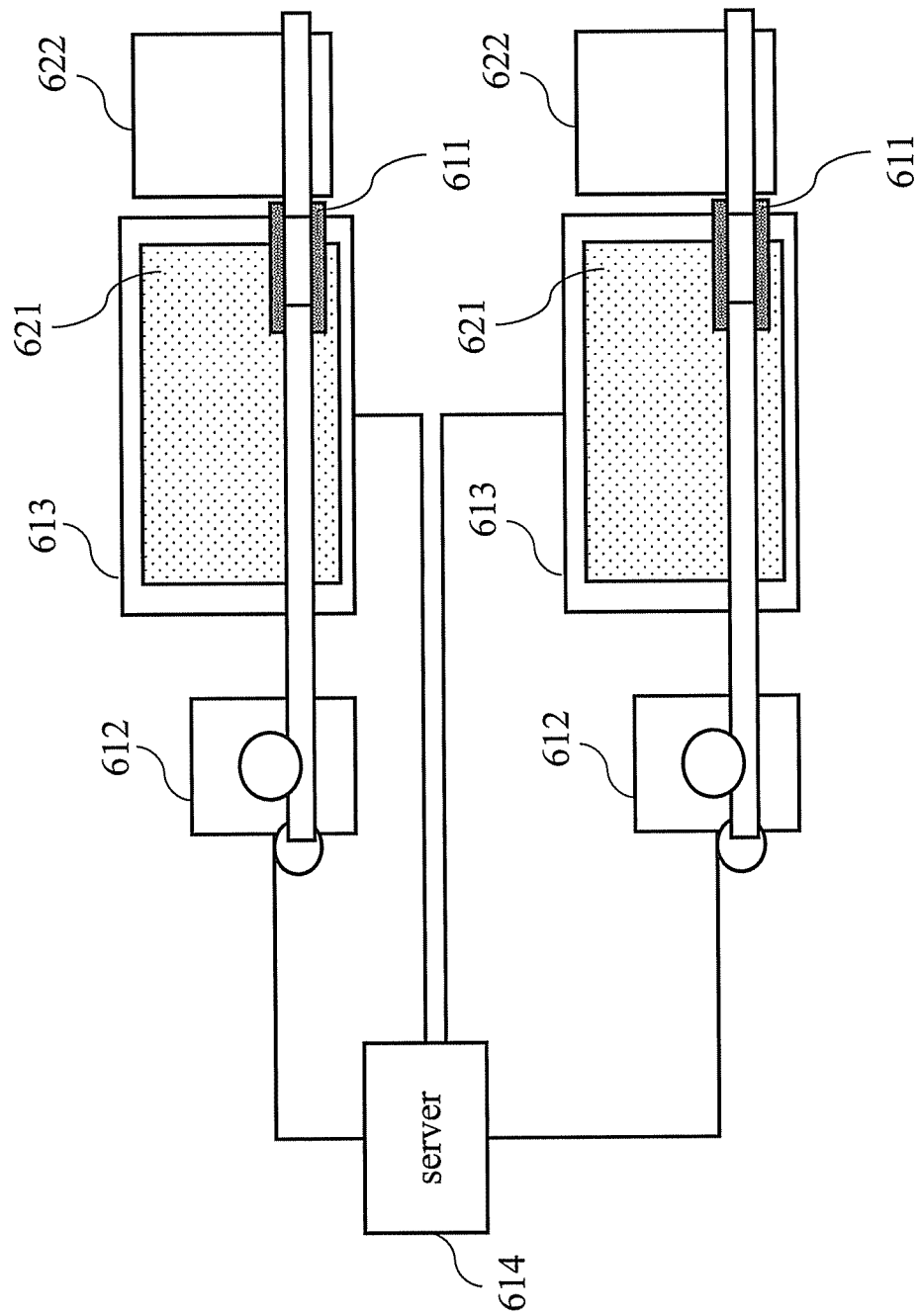
FIG. 6 is a schematic diagram of a state where multiple units under test are simultaneously tested by applying the present invention.

Referring to FIG. 5 and FIG. 6, an embodiment will be set forth to explain the above method. FIG. 5 is a schematic diagram of the fixture device according to the present invention.

In real implementation, a detailed architecture of the fixture (112, 122) may be as what FIG. 5 shows. The fixture device 500 comprises a fixation element 511, linear sliding rails (512, 513), a controller 514 and a stepping motor 515. The fixation element 511 is used to fix the unit under test (not shown). The linear sliding rails (512, 513) may go along with each other to make move possible in a two dimensional space, and may even implement a three dimensional space move by adding a linear sliding rail. The controller 514 controls the stepping motor 515 to move according to the second or third control signals.

FIG. 6 is a schematic diagram of a state where multiple units under test are simultaneously tested by applying the present invention is shown. In real implementation, as shown in FIG. 6, multiple test systems is disposed are used to automatically test multiple unit under test 621. The smart interaction device 611 is used to scan the barcode or two dimensional code, take the picture of the display 622 of the unit under test 621 for processing.

Furthermore, the smart interaction device 611 even controls a sound receiving element, such as a microphone, and a loudspeaker, such as a horn, to record the sound of the unit under test 621, or broadcast a sound to be recorded by the unit under test 621. The smart interaction device 611 may communicate wireless with the test terminal 613 or the server 614 through a wireless communications device. The fixture device 612 and the server 614 are communicated with each other and control the stepping motor to move to a designated position.

The test terminal 613 is used to execute an automatic test process, and receive a message from the smart interaction device 611, such as the barcode, picture and sound. The test terminal 613 may directly or indirectly control the smart interaction deice 611, and even transmit the message to the server 614. The server 614 may, in real implementation, enable the multiple smart interaction devices 611, fixture devices 612, and test terminals 613 to register, be cancelled, and acquire the associated messages, such as an ID code, so as to control these devices 611, 612, 613. The server 614 may also screen out the script, transmit the control signal to the smart interaction device 611 and acquire the feedback message, such as the barcode, and issue a control signal to the fixture device 612 to control the stepping motor, so as to position the smart interaction device 611. Furthermore, the server 614 may also transmit the test script screened out to the test terminal 613 for the automatic test process.

In view of the above, the system and method of the present invention has the difference as compared to the prior art that the present invention drives the fixture device, smart interaction device and test terminal through a control signal, so that the smart interaction device installed in the fixture device scans the barcode and picture of the unit under test and records the sound and plays the sound preset in the smart interaction device, so as to provide the test terminal to verify when executing an automatic test process to generate a test result, whereby solving the issue encountered in the prior art and achieving in a result of promotion of a test efficiency.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An automatic test system, comprising:
    a smart interaction device, receiving a first control signal and scanning a barcode of a unit under test, taking a picture of the unit under test, recording a sound generated by the unit under test and playing a sound preset in the smart interaction device according to the first control signal;
    a fixture device, receiving a second control signal and moving the smart interaction device installed therein according to the second control signal;
    a test terminal, receiving and executing a test script to automatically test the unit under test, and verifying the barcode, picture and sound of the unit under test received from the smart interaction device to generate a test result; and
    a server, transmitting the test script pre-stored in the test script to the test terminal, generating the first and second control signals, and transmitting the first and second control signals to the smart interaction device and the fixture device, respectively.

2. The automatic test system as claimed in claim 1, wherein the fixture device comprises a fixation element, a linear sliding rail, a controller and a stepping motor for enabling the smart interaction device to move in a two dimensional space or a three dimensional space.

3. The automatic test system as claimed in claim 1, wherein the smart interaction device comprises a smart cell phone, a digital personal assistant and a tablet computer comprises a photographing element, a sound receiving element, a loudspeaker, and a wireless transmitter device.

4. The automatic test system as claimed in claim 1, wherein the smart interaction device is wirelessly communicated with the test terminal, the smart interaction device and the server.

5. An automatic test system, comprising:
    a smart interaction device, receiving a first control signal and a second control signal, and scanning a barcode of a unit under test according to the first control signal, and taking a picture of the unit under test, recording a sound generated by the unit under test and playing a sound preset in the smart interaction device according to the second control signal;
    a fixture device, receiving a third control signal and moving the smart interaction device installed therein according to the third control signal;
    a test terminal, receiving and executing a test script to automatically test the unit under test, and generating a second test signal to receive the picture and sound of the unit under test received from the smart interaction device to generate a test result; and
    a server, generating the first control signal and transmitting the first control signal to the smart interaction device, receiving the barcode of the unit under test from the smart interaction device to screen out the test script to be transmitted to the test terminal, and generating the third control signal to transmit to the fixture device.

6. The automatic test system as claimed in claim 5, wherein the fixture device comprises a fixation element, a linear sliding rail, a controller and a stepping motor for enabling the smart interaction device to move in a two dimensional space or a three dimensional space.

7. The automatic test system as claimed in claim 5, wherein the smart interaction device comprises a smart cell phone, a digital personal assistant and a tablet computer comprises a photographing element, a sound receiving element, a loudspeaker, and a wireless transmitter device.

8. The automatic test system as claimed in claim 5, wherein the smart interaction device is wirelessly communicated with the test terminal, the smart interaction device and the server.

9. An automatic test method, applied onto an environment having a smart interaction device, a fixture device, a test terminal and a server, comprising steps of:
    transmitting a test script presorted by the server to the test terminal, and generating a first control signal and a second control signal to transmit the first and second control signals to the smart interaction device and the fixture device, respectively;
    receiving the first control signal by the smart interaction device and scanning a barcode of a unit under test, taking a picture of the unit under test, recording a sound generated by the unit under test, and playing a sound preset in the smart interaction device according to the first control signal;
    receiving the second signal by the fixture device and moving the smart interaction device installed in the fixture device according to the second control signal; and
    receiving and executing the test script by the test terminal to automatically test the unit under test, and verifying the barcode, picture and sound of the unit under test received from the smart interaction device to generate a test result.

10. The automatic test method as claimed in claim 9, wherein the fixture device comprises a fixation element, a linear sliding rail, a controller and a stepping motor for enabling the smart interaction device to move in a two dimensional space or a three dimensional space.

11. The automatic test method as claimed in claim 9, wherein the smart interaction device comprises a smart cell phone, a digital personal assistant and a tablet computer comprises a photographing element, a sound receiving element, a loudspeaker, and a wireless transmitter device.

12. The automatic test method as claimed in claim 9, wherein the smart interaction device is wirelessly communicated with the test terminal, the smart interaction device and the server.

13. An automatic test method, applied onto an environment having a smart interaction device, a fixture device, a test terminal and a server, comprising steps of:
generating a first control signal and transmitting the first control signal to the smart interaction device, and generating a third control signal and transmitting the third control signal to the fixture device;
moving the smart interaction device installed in the fixture device according to the third control signal by the fixture device;
scanning a barcode of a unit under test by the smart interaction device according to the first control signal;
receiving the barcode of the unit under test from the smart interaction device by the server to screen out a test script to be transmitted to the test terminal;
receiving and executing the test script by the test terminal to automatically test the unit under test, and generating a second control signal to the smart interaction device;
taking a picture of the unit under test, recording a sound generated by the unit under test and playing a sound preset in the smart interaction device by the smart interaction device according to the second control signal; and
receiving and verifying the picture and sound from the smart interaction device by the test terminal to generate a test result.

14. The automatic test method as claimed in claim 13, wherein the fixture device comprises a fixation element, a linear sliding rail, a controller and a stepping motor for enabling the smart interaction device to move in a two dimensional space or a three dimensional space.

15. The automatic test method as claimed in claim 13, wherein the smart interaction device comprises a smart cell phone, a digital personal assistant and a tablet computer comprises a photographing element, a sound receiving element, a loudspeaker, and a wireless transmitter device.

16. The automatic test method as claimed in claim 13, wherein the smart interaction device is wirelessly communicated with the test terminal, the smart interaction device and the server.

* * * * *